United States Patent [19]

Burgoyne, Jr. et al.

[11] Patent Number: 4,990,667
[45] Date of Patent: Feb. 5, 1991

[54] ALKYLATED 1,1-BIS(4-AMINOPHENYL)-1-PHENYL-2,2,2-TRIFLUOROETHANES

[75] Inventors: William F. Burgoyne, Jr., Emmaus; Michael Langsam, Allentown, both of Pa.

[73] Assignee: Air Products and Chemicals, Inc., Allentown, Pa.

[21] Appl. No.: 471,916

[22] Filed: Jan. 29, 1990

[51] Int. Cl.$^5$ .............................................. C07C 321/00
[52] U.S. Cl. .................................................... 564/335
[58] Field of Search ........................ 564/330, 332, 335

[56] References Cited

U.S. PATENT DOCUMENTS

| | | | |
|---|---|---|---|
| Re. 30,351 | 7/1980 | Hoehn et al. | 55/16 |
| 3,822,202 | 7/1974 | Hoehn | 210/23 |
| 3,828,071 | 8/1974 | Kast et al. | 564/335 X |
| 4,378,400 | 3/1983 | Makino et al. | 428/220 |
| 4,705,540 | 11/1987 | Hayes | 55/16 |
| 4,717,393 | 1/1988 | Hayes | 55/16 |
| 4,717,394 | 1/1988 | Hayes | 55/16 |
| 4,769,399 | 9/1988 | Schenz | 523/123 |

FOREIGN PATENT DOCUMENTS 62-112372 11/1988 Japan.

OTHER PUBLICATIONS

NASA Tech. Bull., cited and supplied by applicants.
Kim et al., "Reverse Remselectivity of $N_2$ over $CH_4$ in Aromatic Polyimides," J. Appl. Poly. Sci., vol. 34, (1987), p. 1767.
M. Salame, "Prediction of Gas Barrier Properties of High Polymers," Poly. Ing. Sci., vol. 26, p. 1543 (1986).
W. D. Krag et al, "Synthesis of Multifunctional Triarylfluoroethanes.1.Condensation of Fluoro Ketones," J. Org. Chem., vol. 42, No. 7 (1977) pp. 1186–1189.

Primary Examiner—Robert V. Hines
Attorney, Agent, or Firm—Mark L. Rodgers; James C. Simmons; William F. Marsh

[57] ABSTRACT

Diamine compounds having the structural formula:

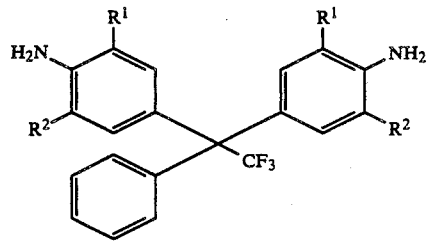

wherein $R^1$ and $R^2$ are independently methyl, ethyl or isopropyl groups, can be used in preparing various polymers which are useful in gas separation membranes. The combined effect of alkyl substituents ortho to the amino groups along with the specific bridging group imparts useful properties to polymeric membranes formed with these diamines.

4 Claims, No Drawings

ALKYLATED 1,1-BIS(4-AMINOPHENYL)-1-PHENYL-2,2,2-TRIFLUOROETHANES

TECHNICAL FIELD

The present invention relates to ortho-alkylated bisanilines which are useful in polymer preparations for gas membrane applications.

BACKGROUND OF THE INVENTION

There is a need for improved polymeric materials that are highly permeable, yet may under certain circumstances, provide selective separation of various gas combinations. Such materials would especially be useful in commercial, non-cryogenic gas separation processes.

The commercial application for gas separation devices based on polymeric materials relies, in part, on maximizing the overall gas flux through the membrane. P. H. Kim, et al., J. Appl. Poly. Sci., 34 1761 (1987), reported that the gas flux for a membrane is relatable to the average space between the polymer chains. In addition, they indicated that the density of the polymer is also related to the overall gas flux. The problem, in part, for these commercial applications is to identify polymers with very high flux and with good thermomechanical properties. It has generally been observed that to achieve high overall flux requires having a polymer with low chain-chain interactions. This can be exemplified by polymers such as poly(dimethylsiloxane) or poly(4-methyl-1-pentene). These materials have rather high gas flux values. These high flux materials have, because of their low chain-chain interaction, low glass transition temperatures (Tg). As a consequence, these materials require either special processing conditions to build in chemical and physiochemical crosslinking or they can be used only at rather low application temperatures. By contrast, polymers with strong chain-chain interactions have rather high Tg values and have usually exhibited rather low gas flux.

Polyimides, which generally have strong chain-chain interactions and have high Tg values, have been reported to have good gas flux values for certain specific structures. Specifically, U.S. Pat. No. 3,822,202 (1974), U.S. Pat. No. Re. 30,351 (1980) discloses a process for separating fluids using a semipermeable membrane made from polyimides, polyesters or polyamides. The repeating units of the main polymer chain of these membranes are distinguished in that such repeating units have at least one rigid divalent subunit, the two main chain single bonds extending from which are not colinear, is sterically unable to rotate 360° around at least one of these bonds, and has 50% or more of its main chain atoms as members of aromatic rings.

U.S. Pat. No. 4,705,540 discloses a highly permeable aromatic polyimide gas separation membrane and processes for using said membrane. The membrane is an aromatic polyimide membrane in which the phenylenediamines are rigid and are substituted on a essentially all of the positions ortho to the amino substituents, and the acid anhydride groups are essentially all attached to rigid aromatic moieties.

U.S. Pat. Nos. 4,717,393 and 4,717,394 teach polymeric membranes and processes using the membranes for separating components of the gas mixture. The membranes disclosed in both of these patents are semiflexible, aromatic polyimides, prepared by polycondensation of dianhydrides with phenylenediamines having alkyl substituents on all ortho positions to the amine functions, or with mixtures of other, non-alkylated diamines, some components have substituents on all positions ortho to the amine functions. It is taught that membranes formed from this class of polyimides exhibit improved environmental stability and gas permeability, due to the optimization of the molecular free volume in the polymer. It is also taught that such membranes can be photochemically crosslinked, which in some instances results in a better performing membrane.

U.S. Pat. No. 4,378,400 discloses gas separation membranes formed from aromatic polyimides based upon biphenyltetra-carboxylic dianhydride for separating various gas mixtures. Japanese patent application 62-112372 discloses a polymeric membrane with an aromatic condensed polyimide as the film material.

M. Salame in Poly. Eng. Sci., 26 1543 (1986) developed a predictive relationship for oxygen permeability coefficient [(PO$_2$)] and polymer structure. In the publication he demonstrates the group contributions of various structural portions of a polymer to P(O$_2$) values. In particular he indicates the presence of an aromatic group, such as phenyl, in place of a methylene (—CH$_2$—) decreases the P(O$_2$) values for a pair of comparative polymers.

U.S. Pat. No. 4,769,399 discloses an adhesive composition which is the reaction product of an admixture of an effective amount of a phenoxy resin, at least one epoxy resin and a fluorene curative. Additionally, European patent application 203828 (1986) also discloses a fluorene compound for use in adhesives.

W. D. Kray and R. W. Rosser in an article entitled "Synthesis of Multifunctional Triarylfluoroethanes .1. Condensation of Fluoro Ketones" ' J. Org. Chem. 42 No.7 (1977) 1186–9 teach a synthesis technique for making compounds having the structural formula:

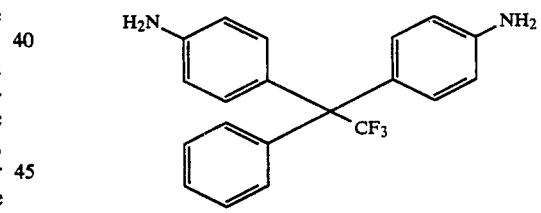

SUMMARY OF THE INVENTION

Novel alkylated 1,1-bis(4-aminophenyl)-1-phenyl-2,2,2-trifluoroethanes have been found which are useful in preparing various polymers for gas separation membranes. These diamine compounds can be represented by the structural formula:

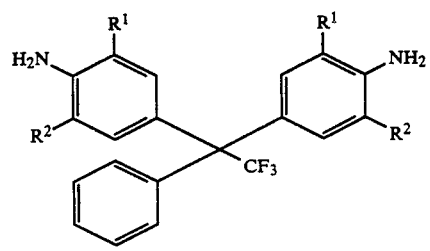

wherein $R^1$ and $R^2$ are independently methyl, ethyl or isopropyl groups.

The presence of the optimum combination of a 1-phenyl-2,2,2-trifluoroethylidene bridging group and the steric effects of specific alkyl groups ortho to the amine function, impart desirable properties to membranes formed from polymers prepared from these diamines. Specifically, such polymer membranes typically exhibit increased oxygen permeance, increased average main chain spacing and decreased average polymer density compared to membranes formed from similar polymers without these specific diamines.

DETAILED DESCRIPTION OF THE INVENTION

The present invention is drawn to novel alkylated 1,1-bis{4-aminophenyl}-1-phenyl-2,2,2-trifluoroethanes represented by the structural formula:

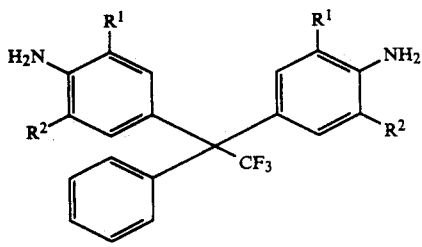

wherein $R^1$ and $R^2$ are independently methyl, ethyl or isopropyl groups.

The above diamines are prepared by the acid-catalyzed condensation of the appropriately substituted aniline with 1,1,1-trifluoroacetophenone, and when polymerized with appropriate dielectrophiles, provide polymers which are useful as gas separation membranes. These diamines can be described as ortho-alkylated bisanilines wherein the bridging group is a 1-phenyl-2,2-trifluoroethylidene moiety. The combined effect of the specific substituents ortho to the amino groups along with the particular bridging group results in diamine monomers which are extremely useful in polymer preparations for gas membrane applications. Polymers, such as polyimides, prepared from these diamines are effective as high flux gas separation membranes, in part, due to restricted rotation and/or low Van der Waal energy for the bridging group and the steric bulk of the alkyl groups ortho to the diamine functional groups. These physical properties result in polymer membranes which exhibit high oxygen permeability, high average main chain spacing and decreased average polymer density when compared to similar polymers made from prior art diamines.

In the diamine structure, both ortho positions to each amino group are alkyl groups selected from methyl, ethyl and isopropyl. In a preferred embodiment, at least one ortho position to each amino group is isopropyl and most preferably all four ortho positions are isopropyl. Accordingly, the preferred diamine of this invention is 1,1-bis(3,5-diisopropyl-4-aminophenyl)-1-phenyl-2,2,2-trifluoroethane. A key feature of this invention is the presence of alkyl groups at both of the ortho positions to each amino group. It has been shown that if hydrogen is substituted for an alkyl group at any of these ortho positions, the diamine does not exhibit the desired properties. While these diamines are useful in forming polyimide gas separation membranes, they are also useful in forming other polymers for membrane and other applications, as well as for other uses, such as in adhesive compositions.

EXPERIMENTAL

Preparation of 1,1-Bis(4-aminoaryl)-1-phenyl-2,2,2-trifluoroethanes

The following general procedure was used to prepare the 1,1-bis (4-aminoaryl)-1-phenyl-2,2,2-trifluoroethanes. Specific product yields and physical properties, along with the specific diamines synthesized are outlined in Table 1. All compounds provided satisfactory spectral and elemental analysis.

A 50.00 g (0.333 mol) portion of trifluoromethanesulfonic acid was slowly added to 1.75 moles of an arylamine, corresponding to the desired bisaniline product, contained in a one liter, three necked flash with mechanical stirring. After thorough mixing had occurred. 43.53g (0 250 mol) of 1,1,1-trifluoroacetophenone was added. The mixture was then heated to 155° C. for 17 hrs. under an atmosphere of nitrogen with continuous stirring. After which time, the reaction vessel was fitted with a Claisen distillation head and the excess arylamine along with some of the acid were removed via vacuum distillation. The residual product was cooled below 80° C. then neutralized with a solution of 40.0 g (1.00 mol) of sodium hydroxide in 200 ml of water. A 800 g portion of toluene was then added with vigorous stirring. After 5 min., stirring was discontinued and the layers were separated. The organic layer was dried over anhydrous magnesium sulfate then the toluene was evaporated. Polymer grade diamine was obtained from the residue after recrystallization followed by vacuum drying at 80°-100° C./5 mm Hg for 24 hours.

TABLE 1

Preparation of 1,1-Bis(4-aminoaryl)-1-phenyl-2,2,2-trifluoroethanes

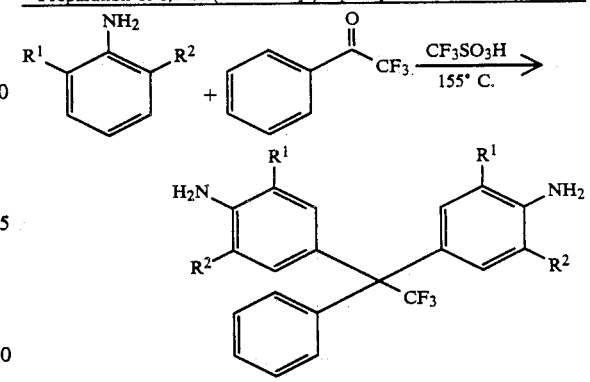

| | Diamine | | | % Isolated | |
|---|---|---|---|---|---|
| Sample | $R^1$ | $R^2$ | Solvent | Yield | mp °C. |
| 1* | H | H | toluene/hexane | 80.0 | 214–216 |
| 2 | $CH_3$ | $CH_3$ | toluene/hexane | 64.5 | 171–173 |
| 3 | $CH_3$ | $i\text{-}C_3H_7$ | toluene | 44.6 | 160–162 |
| 4 | $i\text{-}C_3H_7$ | $i\text{-}C_3H_7$ | toluene/hexane | 66.0 | 182–185 |

*Comparative sample

EXAMPLES 1–4

The diamine compounds synthesized above were reacted with 6F-dianhydride to form polyimides in accordance with the procedures set out in U.S. patent application Ser. No. 07/316,214. The resultant polyimides were cast as thin film membranes and tested for oxygen permeance ($\bar{P}_{O_2}$) and $O_2/N_2$ selectivity ($\alpha O_2/N_2$). The results of these tests, along with the specific polyimide structures are set out in Table 2 below.

TABLE 2

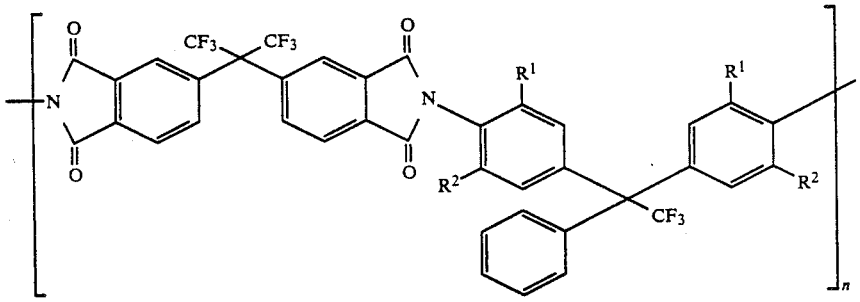

| Example | $R^1$ | $R^2$ | $\bar{P}_{O2}$ | $\alpha(O_2N_2)$ |
|---|---|---|---|---|
| 1* | H | H | 3.83 | 5.0 |
| 2 | $CH_3$ | $CH_3$ | 25.5 | 3.0 |
| 3 | $CH_3$ | $i$-$C_3H_7$ | 57.2 | 3.5 |
| 4 | $i$-$C_3H_7$ | $i$-$C_3H_7$ | 80.0 | 3.22 |

*Comparative example

From the results reported in Table 2 above, it is clearly shown that the diamines of the present invention can be used to form polyimide membranes which exhibit significantly higher oxygen permeance than polyimides formed from prior art diamines.

Having thus described the present invention, what is now deemed appropriate for Letters Patent is set out in the following appended claims.

What is claimed is:

1. A diamine having the structural formula:

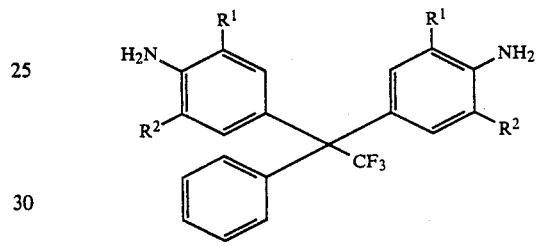

wherein $R^1$ and $R^2$ are independently methyl, ethyl, or isopropyl groups.

2. A diamine in accordance with claim 1 wherein $R^1$ is isopropyl.

3. A diamine in accordance with claim 2 wherein $R^2$ is isopropyl.

4. A diamine in accordance with claim 2 wherein $R^2$ is methyl.